(12) United States Patent
Otsubo

(10) Patent No.: US 8,349,117 B2
(45) Date of Patent: Jan. 8, 2013

(54) ABSORBENT WEARING ARTICLE AND PROCESS OF MAKING THE SAME

(75) Inventor: Toshifumi Otsubo, Kagawa-ken (JP)

(73) Assignee: Uni-Charm Corporation, Shikokuchuo-shi (JP)

(*) Notice: Subject to any disclaimer, the term of this patent is extended or adjusted under 35 U.S.C. 154(b) by 198 days.

(21) Appl. No.: 12/835,930

(22) Filed: Jul. 14, 2010

(65) Prior Publication Data

US 2010/0276070 A1  Nov. 4, 2010

Related U.S. Application Data

(62) Division of application No. 11/942,948, filed on Nov. 20, 2007, now Pat. No. 8,057,451.

(30) Foreign Application Priority Data

Dec. 1, 2006  (JP) .................................. 2006-326231

(51) Int. Cl.
 *B32B 37/00* (2006.01)
 *B32B 37/02* (2006.01)
 *B32B 37/14* (2006.01)
 *B32B 37/16* (2006.01)
 *B32B 38/00* (2006.01)
 *B32B 38/04* (2006.01)
 *B32B 38/10* (2006.01)

(52) U.S. Cl. ........ 156/265; 156/250; 156/252; 156/253; 156/256; 156/264

(58) Field of Classification Search ................ 156/250, 156/252, 253, 256, 264, 265
See application file for complete search history.

(56) References Cited

U.S. PATENT DOCUMENTS

| | | | |
|---|---|---|---|
| 4,720,415 A * | 1/1988 | Vander Wielen et al. | 428/152 |
| 7,604,624 B2 | 10/2009 | Veith et al. | |
| 2004/0243083 A1 | 12/2004 | Matsuda et al. | |
| 2004/0243089 A1 * | 12/2004 | Veith et al. | 604/385.22 |
| 2005/0010186 A1 | 1/2005 | Otsubo et al. | |
| 2005/0126689 A1 * | 6/2005 | Thorson et al. | 156/164 |

FOREIGN PATENT DOCUMENTS

JP  2002-095692  4/2002

OTHER PUBLICATIONS

Otsubo T., U.S. Office Action mailed Apr. 1, 2010, directed to U.S. Appl. No. 11/942,948; 6 pages.
Otsubo T., U.S. Office Action mailed Sep. 8, 2010, directed to U.S. Appl. No. 11/942,948; 6 pages.
Otsubo, U.S. Office Action mailed Feb. 4, 2011, directed to related U.S. Appl. No. 11/942,948; 7 pages.

* cited by examiner

*Primary Examiner* — Mark A Osele
*Assistant Examiner* — Christopher C Caillouet
(74) *Attorney, Agent, or Firm* — Morrison & Foerster LLP

(57) ABSTRACT

An absorbent wearing article including an air permeable and liquid-impervious backsheet and a liquid-retentive absorbent structure placed on the backsheet. An outer sheet has having elastic members is placed on and bonded to a surface of the backsheet opposed to its surface bonded to the absorbent structure. The outer sheet has the elastic members intermittently bonded under tension thereto, and is formed in a region thereof facing the absorbent structure with an opening. The elastic members extend laterally under tension from a peripheral edge of the opening beyond the absorbent structure and the first backsheet is exposed through the opening.

5 Claims, 3 Drawing Sheets

ABSORBENT WEARING ARTICLE AND PROCESS OF MAKING THE SAME

CROSS-REFERENCE TO RELATED APPLICATIONS

This application is a divisional application of U.S. patent application Ser. No. 11/942,948, filed Nov. 20, 2007, which claims priority under 35 U.S.C. §119 to Japanese Patent Application No. 2006-326231, filed Dec. 1, 2006, the contents of which are incorporated herein by reference in their entirety.

BACKGROUND OF THE INVENTION

The present invention relates to an absorbent wearing article and particularly to such an article including elastic members circumferentially extending around front and rear waist regions of the wearer (referred to hereinafter sometimes as fit gathers).

There have already been proposed absorbent wearing articles provided with the fit gathers circumferentially extending around the front and rear waist regions to improve fit of the article around the wearer's waist.

For example, Japanese Unexamined Patent Application Publication No. 2002-95692, which is hereby incorporated by reference in its entirety herein, discloses an absorbent article comprising a liquid-pervious topsheet, a liquid-impervious backsheet and a liquid-retentive absorbent structure interposed between these two sheets so as to define a front waist region, a rear waist region and a crotch region wherein the front waist region and/or the rear waist region is or are provided with a plurality of waist elastic members extending in a transverse direction at predetermined intervals. In a region occupied by the absorbent structure, these waist elastic members have elasticity thereof restrained and, outside the opposite side edges of the absorbent structure, these elastic members are fixed to the components of the absorbent wearing article by means of first fastening means so that the elasticity thereof is activated. In the vicinity of borders defined between the regions in which the elasticity is restrained and the regions in which the elasticity is activated, the waist elastic members are fixed to the components of the absorbent article by means of second fastening means.

In the absorbent article disclosed in the aforesaid Publication, the waist elastic members are interposed between two sheets and a tensile stress as well as a draw ratio at which the waist elastic members are attached to the article can be freely determined so that the absorbent article such as a disposable diaper improved in fit, absorption capacity and leakage barrier performance may be provided. However, according to the technique disclosed in the aforesaid Publication, the waist elastic members are not bonded to those two sheets in the region occupied by the absorbent structure and cut off so that the elasticity of the waist elastic members is not activated. In the vicinity of borders defined between the regions in which the elasticity is restrained and the regions in which the elasticity is activated, the waist elastic members are fixed to the components of the absorbent article. With such arrangement, the segments of the waist elastic members having the elasticity restrained are left to contract and to be shortened. Those two sheets are free from the contraction and left to cover the absorbent structure.

Consequentially, the air permeability of the absorbent structure to the ambient air may be deteriorated due to two sheets covering the absorbent structure. In addition, a graphic or logo sometimes printed on the front waist region or the rear waist region of the absorbent wearing article may lose a desired visual quality.

SUMMARY OF THE INVENTION

In view of the problems left by the prior art unsolved behind as have been described above, it is an object of the present invention to provide an absorbent wearing article having fit gathers improved so that an absorbent structure has a high air permeability to ambient air and a graphic or logo printed on the article maintains a high visual quality and a process for making the same.

There are provided an absorbent wearing article and a process for making the same.

According to the first aspect of the present invention, an outer sheet having elastic members and an area larger than that of a first backsheet is placed on and bonded to a surface of the first backsheet opposed to its surface bonded to an absorbent structure, the outer sheet has the elastic members intermittently bonded under tension thereto and is formed in a region thereof facing the absorbent structure with an opening, the elastic members extend laterally under tension from a peripheral edge of the opening beyond opposite side edges of the absorbent structure and the first backsheet is exposed through said opening.

According to the second aspect of the present invention comprises the steps of continuously feeding continuous elastic members in a direction parallel to a machine direction to continuous outer sheet continuously fed in the machine direction while the continuous elastic members are intermittently bonded under tension to the continuous outer sheet, making cuts extending orthogonally to the machine direction in the continuous outer sheet having the continuous elastic members bonded thereto so that the continuous elastic members are at least partially chopped off, and bonding the side of the absorbent structure facing the first backsheet to the continuous outer sheet.

According to the present invention, the outer sheet including the elastic members (so-called fit gathers) is formed in its region opposed the absorbent structure with the opening through which the first backsheet is exposed so that the first sheet is exposed directly to ambient air. In this way, the absorbent wearing article assuring a high air permeability of the absorbent structure to ambient air. In addition to such high 20 air permeability of the absorbent structure, a graphic or logo may be printed on the first backsheet assures its visual quality because the first backsheet is exposed through the opening as has previously been described.

BRIEF DESCRIPTION OF THE DRAWINGS

The invention will become more readily apparent from the Detailed Description of the Invention, which proceeds with reference to the drawings, in which.

Figure 1:
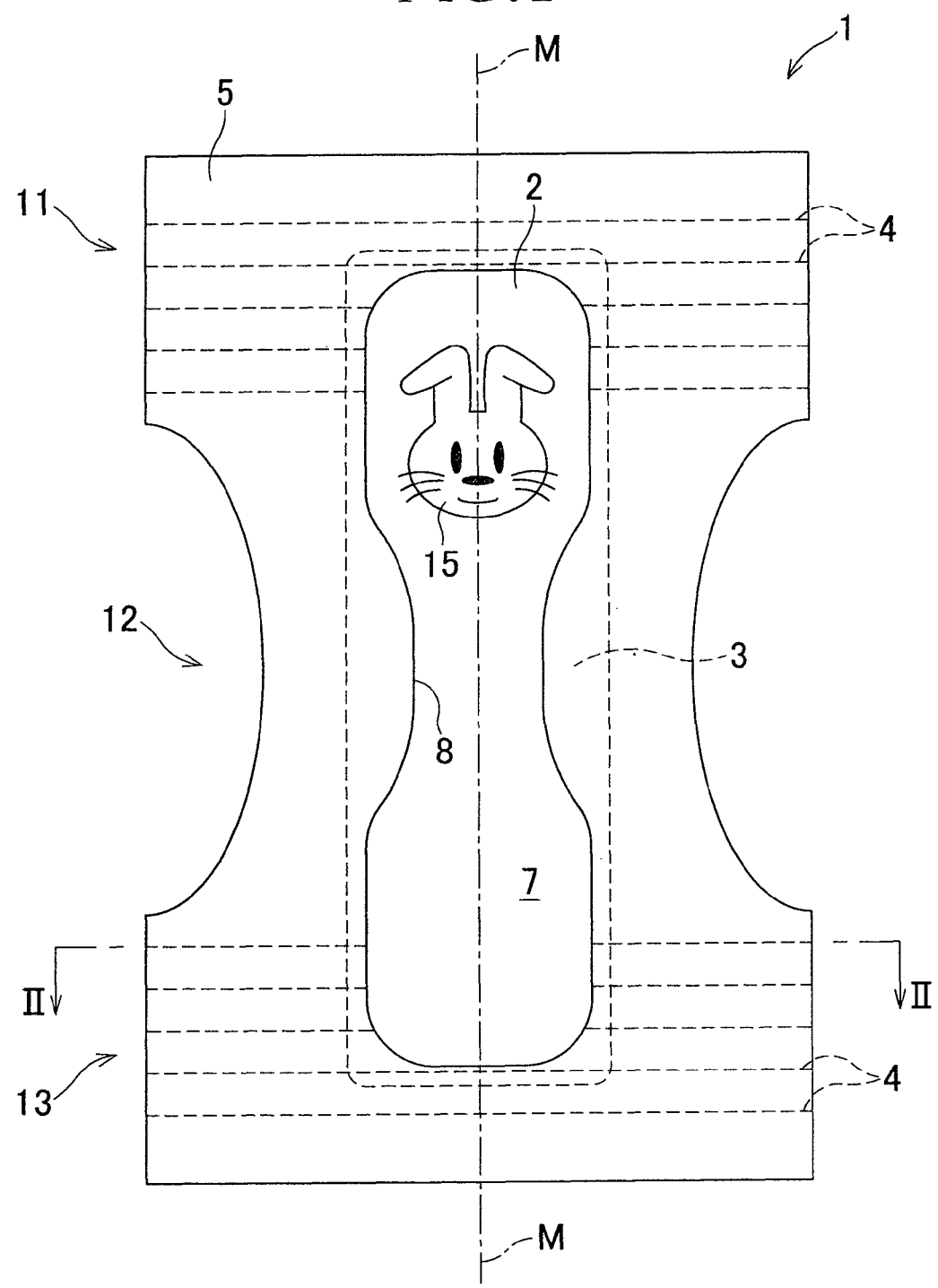
FIG. 1 illustrates a diaper developed and flattened.

In the figures, elements that are repeatedly illustrated are consistently identified by a single reference numeral.

DETAILED DESCRIPTION OF THE INVENTION

Figure 2:
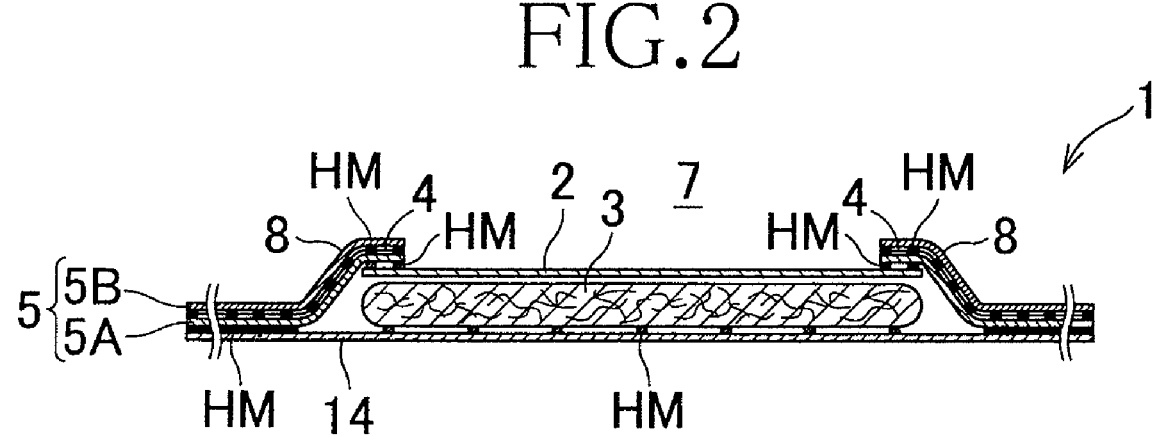
FIG. 2 schematically illustrates the diaper in a sectional view taken in parallel to elastic members.

Taking a diaper 1 as an example, an embodiment of the absorbent wearing article according to the present invention will be described with reference to the accompanying drawings wherein FIG. 1 is a plan view of the diaper 1 developed and flattened as viewed from its outer surface, i.e., its surface opposed to its surface facing the wearer's skin and FIG. 2 is a sectional view taken along the line II-II in FIG. 1.

The diaper 1 developed and flattened has a shape which is symmetric about a center line M and divided by invisible lines extending orthogonally to the center line M to define a front waist region II, a crotch region 12 and a rear waist region 13 in this order. Referring to FIG. 1, an outer sheet 5 formed with an opening 7 and a first backsheet 2 is exposed in this opening 7.

The first backsheet 2 is smaller than the outer sheet 5 and an absorbent structure 3 having an area smaller than that of the first backsheet 2 is bonded to the backside of the first backsheet 2. In the front waist region 11 and the rear waist region 13, the outer sheet 5 is provided on the backside thereof with elastic members 4 comprising a plurality of rubber strings extending under tension orthogonally to the center line M so that a fit of the diaper 1 around the diaper wearer's waist may be improved.

The opening 7 extends in the crotch region 12 and further into the front and rear waist regions 11, 13 symmetrically about the center line M. The absorbent structure 3 bonded to the first backsheet 2 also extends in a manner similar to the opening 7 so as to cover this opening 7. On both sides of the absorbent structure 3, the elastic members 4 laterally extend under tension from a peripheral edge 8 of the opening 7 beyond the opposite side edges of the absorbent structure 3. In the opening 7, the first backsheet 2 and a graphic printed thereon is exposed. Though not illustrated, it is possible to divide the opening 7 in two or more zones unless the graphic is partially masked.

FIG. 2 is a schematic sectional view of the diaper 1 taken along the line II-II, i.e., along the elastic members 4.

The outer sheet 5 of the diaper 1 comprises a second backsheet 5A and an outer covering sheet 5B. The elastic members 4 are sandwiched between these two sheets 5A, 5B and intermittently bonded thereto by means of hot melt adhesive HM. The absorbent structure 3 is bonded through the intermediary of the first backsheet 2 to the second backsheet 5A constituting the outer sheet 5 by means of hot melt adhesive HM.

Each of the first backsheet 2, the second backsheet 5A and the outer covering sheet 5B is made of a breathable and liquid-resistant or liquid-impervious sheet wherein the outer covering sheet 5B defines the outside of the diaper 1. A liquid-pervious topsheet 14 facing the wearer's skin is placed on and bonded to the second backsheet 5A and the absorbent structure 3. More specifically, the topsheet 14 is intermittently bonded to the absorbent structure 3 by means of hot melt adhesive HM. While the topsheet 14 is provided with members of well known art such as leakage barrier cuffs and rubber strings serving to improve a fit of the diaper 1 around the wearer's waist and legs, details of these members will be neither described nor illustrated herein.

The first backsheet 2 and the second backsheet 5A are bonded to each other so as to surround the opening 7 and thereby to avoid an apprehension that body waste such as urine might leak through a gap between these two sheets 2, 5A. Preferably, the peripheral edge 8 of the opening 7 is fully bonded to the first backsheet 2. An area of the opening 7 is dimensioned to be smaller than an area of the absorbent structure 3. Preferably, the opening 7 is formed in a manner that the peripheral edge 8 of the opening 7 is as close as possible to the peripheral edge of the absorbent structure 3 with a margin for bonding left and thereby the opening area is maximized.

As will be apparent from FIG. 2, the elastic members 4 extend under tension to the peripheral edge 8 of the opening 7. Compared to the case in which the elastic members 4 are cut between the second backsheet 5A and the outer covering sheet 5B and contracted these two sheets, it is possible for the construction illustrated by FIG. 2 to obtain the larger opening 7. Thus the first backsheet 2 having the absorbent structure 3 bonded thereto is exposed through the opening 7 and the area of the first backsheet 2 adapted to come in contact with ambient air without being masked by the outer sheet 5 can be maximized. Consequentially, a high permeability of the absorbent structure 3 to ambient air is ensured and a high visibility of the graphic 15 printed on the first backsheet 2 is also ensured since there is nothing which might mask the graphic 15 (See FIG. 1).

The elastic members 4 extend under tension in a direction along which these elastic members 4 bear away from the absorbent structure 3 and, more preferably are extend outward under tension in a direction which is orthogonal to the center line M so as to strain not only the first backsheet 2 itself but also the absorbent structure 3 through the intermediary of this first backsheet 2. Consequentially, it is neither apprehended that the graphic 15 might get wrinkled so as to lose its initial shape as well as its visual quality nor apprehended that the absorbent structure 3 might get wrinkled and body waste such as urine might leak through such wrinkles. In this regard, it is not essential for the present invention to bond the first backsheet 2 directly to the absorbent structure 3 so far as the first backsheet 2 displaying the graphic 15 is free from getting wrinkled. However, even if the first backsheet 2 is indirectly bonded to the absorbent structure 3, the absorbent structure 3 is preferably bonded to the topsheet 14 and/or the second backsheet 5A.

Figure 3:
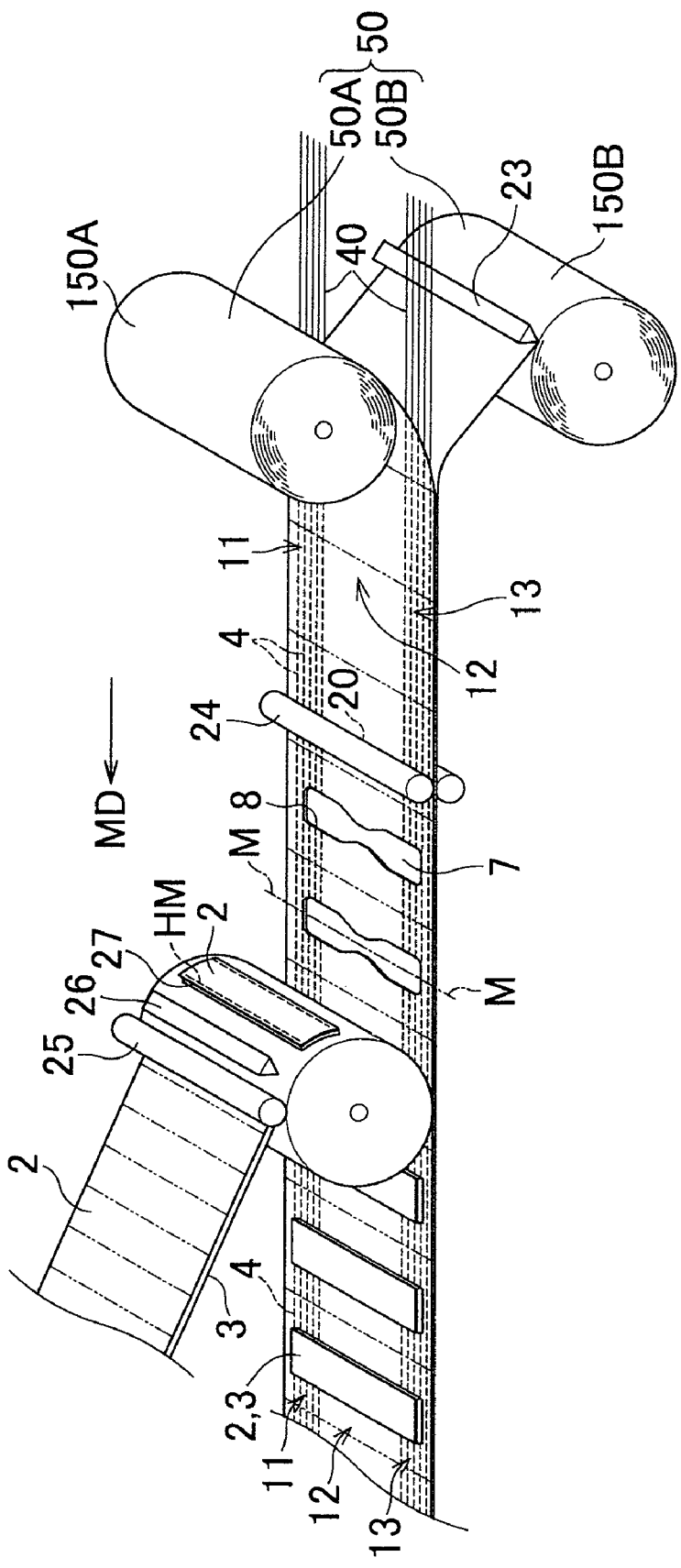
FIG. 3 schematically illustrates a process for making the diaper.

FIG. 3 schematically illustrates a process according to the present invention for making the diaper 1.

The process according to the present invention basically comprises the steps of continuously feeding continuous elastic members 40 comprising a plurality of rubber strings in a direction parallel to a machine direction MD to a continuous outer sheet 50 continuously fed in the machine direction MD while the continuous elastic members 40 are intermittently bonded under tension to the continuous outer sheet 50, making cuts extending orthogonally to the machine direction MD in the continuous outer sheet 50 having the continuous elastic members 40 bonded thereto so that the continuous elastic members 40 are at least partially chopped off and bonding the side of the absorbent structure 3 facing the first backsheet 2 to the continuous outer sheet 50.

The center line M of the diaper 1 obtained by this process is orthogonal to the machine direction MD. The topsheet 14 (which is continuous in the machine direction MD) and the other members (not illustrated in FIG. 3) are bonded, in subsequent steps, to the continuous outer sheet 50 having the absorbent structure 3 bonded thereto and then the assembly obtained in this manner is cut into the individual diapers 1 as finished products.

The process according to the invention starts with continuously feeding the continuous elastic members 40 and bonding to the sections of the continuous outer sheet 50 destined to define the front waist regions 11 and the rear waist regions 13. The continuous outer sheet 50 comprises the continuous second backsheet 50A and the continuous outer covering sheet 50B placed on and bonded to the continuous second backsheet 50A wherein the continuous elastic members 40 are fed so as to be interposed between the continuous second backsheet 50A and the continuous outer covering sheet 50B. Bonding of the continuous elastic members 40 to the outer sheet 50 is achieved by intermittently coating the continuous outer covering sheet 50B with hot melt adhesive HM using a first adhesive coater 23 (not shown) and then placing the continuous elastic members 40 and the continuous second backsheet 50A. Raw fabric for the continuous second backsheet 50A and the continuous outer covering sheet 50B are fed from respective rolls 150A, 150B.

In the next step, the cuts 20 each rectilinearly extending in the direction parallel to the center line M from the front waist region 11 to the rear waist region 13 are made by the cutter 24. As a result, the continuous elastic members 40 are at least partially cut off and the continuous elastic members 40 extending between each pair of the adjacent cuts 20 contract together with the continuous outer sheet 50 so as to form the opening 7. At this moment, the continuous outer sheet 50 remains under a tension which is effective in the direction parallel to the machine direction MD and therefore the continuous elastic members 40 extending between each pair of the adjacent cuts 20 can not fully contract, i.e., remain in a stretched state.

The shape of the opening 7 may be adjusted by appropriately selecting factors such as draw ratio at which the continuous elastic members 40 are feed as well as tension acting upon the continuous outer sheet 50. Instead of making the cuts 20 in the rectilinear fashion, the cuts 20 may be made so as to cut out partially the continuous outer sheet 50 and thereby the shape of the opening 20 may be adjusted. While the opening area of the opening 7 defined by the peripheral edge 8 thereof should be smaller than that of the absorbent structure 3 as has previously been described, the shape of the opening 7 is preferably adjusted so that the peripheral edge 8 of the opening 7 may be as close as possible to the peripheral edge of the absorbent structure 3 and the opening are may be maximized.

Then the first backsheet 2 having the absorbent structure 3 bonded thereto is bonded to the continuous second backsheet 50A by means of hot adhesive HM so that the first backsheet 2 may cover the opening 7.

The absorbent structure 3 and the first backsheet 2 are bonded to each other in the other step and this assembly obtained in this manner is fed in the state of web in preparation for individually cutting. The absorbent structure 3 having the first backsheet 2 bonded thereto is cut by an absorbent structure cutter 25 into individual assemblies by an absorbent structure cutter 25 and opposite side edges extending orthogonally to the machine direction MD of the first backsheet 2 cut in this manner are coated with hot melt adhesive HM by a second adhesive coater 26. The first backsheet 2 may be previously printed with the graphic 15 or logo (not shown).

The absorbent structure 3 is bonded to the first backsheet 2 so as to cover the opening 7 and thereupon the peripheral edge 8 of the opening 7 is fixed in place by means of hot melt adhesive HM applied on the opposite side edges 27 of the first backsheet 2. In this way, the opening 7 is maintained in an opened state and the continuous elastic members 40 are maintained in a stretched state.

If a clearance is left between the peripheral edge 8 of the opening 7 and the first backsheet 2, there may be provided an additional step of bonding using heat welding technique such as heat sealing technique after the absorbent structure 3 has been bonded to the continuous second backsheet 50A.

Alternatively, the process may include the step of coating the continuous outer sheet along the region in which the cuts 20 are to be made inclusive of components extending orthogonally to the machine direction MD with hot melt adhesive. More specifically, on both sides of the region in which the cut 20 is to be made i.e., regions destined to become the peripheral edge 8 may be previously coated with hot melt adhesive HM. In this case, a third adhesive coater (not shown) may be provided on upstream (in the direction opposite to the machine direction MD) of the cutter 24. To avoid a problem that hot melt adhesive might interfere with operation of making the cut 20, a quantity of hot melt adhesive to be coated is preferably limited. Proper quantity of hot melt adhesive HM to be coated may be experimentally adjusted, for example, to a range of 1 to 3 $g/m^2$.

In this way, the first backsheet 2 can be bonded to the absorbent structure 3 with hot melt adhesive HM extending along the peripheral edge 8 of the opening 7 and thereby the peripheral edge 8 can be fixed in place. A quantity of hot melt adhesive HM to be coated on the first backsheet 2 in the subsequent step can be reduced or eliminate the use thereof.

As stock materials for various sheets such as the continuous backsheet 50A, the continuous outer covering sheet 50B and the first backsheet 2, the materials conventionally used in this technical field including nonwoven fabrics, films or breathable films each made of thermoplastic resins may be selectively used. Bonding of these sheets to the continuous elastic members 40 may be carried out by means of hot melt adhesive HM or heat sealing technique. When hot melt adhesive is used, any particular pattern of coating is not specified and the coating pattern such as stripe-, spiral- or dotted-pattern may be selectively used. To make cuts 20, the cutting means of well known art such as rotary cutter, heat seal cutter supersonic cutter or water jet cutter may be selectively used.

Instead of using a plurality of rubber strings as the continuous elastic members 40, a single elasticized plastic film or elasticized nonwoven fabric may be used in the place of the continuous elastic members 40. In this case, the peripheral edge 8 of the opening 7 in the continuous outer sheet 50 may be bonded together with the single nonwoven fabric or the like used in the place of the continuous elastic members 40 to the first backsheet 2 by means of heat sealing technique or hot melt adhesive HM. When the elastic members 4 is replaced by the single nonwoven fabric or the like, such nonwoven fabric or the other is more reliably prevented from peeling off from the peripheral edge 8 of the opening 7 than in the case of the elastic members comprising a plurality of rubber strings even when such nonwoven fabric or the like contract. In the diaper 1 obtained by the process as has been described above, the continuous outer sheet 50 having the continuous elastic members 40 bonded thereto is formed on its side facing the absorbent structure 3 with the opening 7 through which the first backsheet 2 of the absorbent structure 3 is exposed. The opening 7 allows the first backsheet 2 bonded to the absorbent structure 3 to be directly exposed to ambient air. In this way, the diaper 1 is provided, in which a high air permeability of the absorbent structure 3 to the ambient air is ensured. Furthermore, the first backsheet 2 exposed in this manner ensures that the graphic 15 or logo printed thereon maintains a high visibility thereof.

Furthermore, this process allows the continuous outer sheet 50 under tension to be stretched in the direction parallel to the machine direction MD at the moment of making the cuts in the continuous outer sheet 50. In other words, the continuous outer sheet 50 is stretched out to the width of the diaper 1 as the finished product. Consequentially, it is possible to reduce a dimension (as measured in the machine direction) of the raw fabric fed from the roll destined to become a width dimension of the individual diaper 1 with respect to the width dimension of the individual diaper 1. Compared to the case in which no step of making cuts is included, the production rate can be improved and the production cost can be reduced on the assumption that the rate of feed is maximized.

It is also possible to make a plurality of cuts 20 extending along the center line M. For example, if tow cuts 20 spaced from each other along the center line M to form two openings 7, regions of the continuous outer sheet 50 which are continuous in the machine direction MD of the continuous outer sheet 50 can be increased and running of the continuous outer sheet 50 can be stabilized so that the continuous outer sheet 50 can be easily handled.

It is within the scope of the present invention to include all foreseeable equivalents to the elements of the present invention as described with reference to FIGS. 1-3. The examples provided are not to be interpreted as limiting the invention beyond what is claimed.

What is claimed is:

1. A process for making an absorbent wearing article including an air permeable and liquid-impervious first backsheet and a liquid-retentive absorbent structure placed upon said first backsheet, comprising the steps of:
   continuously feeding continuous elastic members in a direction parallel to a machine direction to a continuous outer sheet continuously fed in said machine direction while said continuous elastic members are intermittently bonded under tension to the continuous outer sheet;
   making cuts extending orthogonally to said machine direction in the continuous outer sheet having said continuous elastic members bonded thereto so that said continuous elastic members are at least partially chopped off to form an opening by said cuts enlarged by contraction of said continuous elastic members adjacent to said cuts; and
   bonding the side of said absorbent structure facing said first backsheet to said continuous outer sheet to cover said opening.

2. The process for making the absorbent wearing article according to claim 1, wherein:
   said absorbent wearing article is symmetric about a center line when said absorbent wearing article is developed in a flattened state;
   said absorbent wearing article comprises a front waist region, a crotch region and a rear waist region in this order in a direction parallel to said center line;
   said center line is orthogonal to said machine direction of said continuous outer sheet;
   said continuous elastic members are fed to said front waist region and said rear waist region;
   said cuts are made in a direction parallel to said centerline so as to extend from said front waist region to said rear waist region; and
   the first backsheet of said absorbent structure is bonded to said outer sheet from said front waist region to said rear waist region so as to cover said opening.

3. The process for making the absorbent wearing article according to claim 1, including a step of coating the regions along which said cuts are made with hot melt adhesive in the direction orthogonal to said machine direction before the step of making the cuts in said continuous outer sheet.

4. The process for making the absorbent wearing article according to claim 1, wherein:
   said outer sheet comprises a continuous second backseet bonded to said first backsheet and a continuous outer covering sheet bonded placed upon and bonded to said second backsheet;
   said continuous elastic members are interposed between said continuous second backsheet and said continuous outer covering sheet and bonded thereto; and
   said first backsheet on a side of said first backsheet is bonded to said continuous second backsheet.

5. The process for making the absorbent wearing article according to claim 1, further comprising making a plurality of cuts spaced one from another along said machine direction for forming a plurality of individual diapers from said continuous outer sheet, continuous elastic members and a plurality of absorbent structures.

* * * * *